United States Patent [19]

Burba et al.

[11] Patent Number: 4,968,732
[45] Date of Patent: Nov. 6, 1990

[54] IMIDAZOLYL-UREA COMPOUNDS AND THEIR USE AS CURE ACCELERATORS IN EPOXY RESIN COMPOSITIONS FOR THE PRODUCTION OF MOLDINGS

[75] Inventors: Christian Burba, Herben; Werner Mrotzek, Dortmund, both of Fed. Rep. of Germany

[73] Assignee: Schering Aktiengesellschaft, Bergkamen, Fed. Rep. of Germany

[21] Appl. No.: 498,005

[22] Filed: Mar. 23, 1990

Related U.S. Application Data

[62] Division of Ser. No. 359,099, May 30, 1989, Pat. No. 4,931,529.

[30] Foreign Application Priority Data

May 28, 1988 [DE] Fed. Rep. of Germany ....... 3818214

[51] Int. Cl.$^5$ .................. C08G 59/44; C08G 59/54; C08J 5/24
[52] U.S. Cl. ..................... 523/466; 427/386; 528/94; 528/117; 528/341; 528/407; 525/504
[58] Field of Search ................ 528/94, 117, 341, 407; 525/504; 523/466; 427/386

[56] References Cited

U.S. PATENT DOCUMENTS

| | | | |
|---|---|---|---|
| 3,335,228 | 6/1982 | Beitchman et al. | 528/94 X |
| 3,661,989 | 5/1972 | Nawakowski | 260/553 |
| 3,717,612 | 2/1973 | Babayan | 260/47 |
| 4,355,058 | 10/1982 | Gras et al. | 528/94 X |
| 4,358,571 | 11/1982 | Kaufman et al. | 528/94 X |
| 4,533,715 | 8/1985 | Lee et al. | 528/45 |
| 4,670,533 | 6/1987 | Lauterbach | 528/94 |
| 4,749,729 | 6/1988 | Kohli et al. | 528/94 X |
| 4,797,455 | 1/1989 | Liu et al. | 528/94 X |
| 4,931,529 | 6/1990 | Burba et al. | 528/94 |

FOREIGN PATENT DOCUMENTS

| | | |
|---|---|---|
| 0193068 | 3/1986 | European Pat. Off. |
| 1349709 | 4/1974 | United Kingdom . |

*Primary Examiner*—Earl Nielsen
*Attorney, Agent, or Firm*—Scully, Scott, Murphy & Presser

[57] ABSTRACT

This invention is directed to a compound of the formula

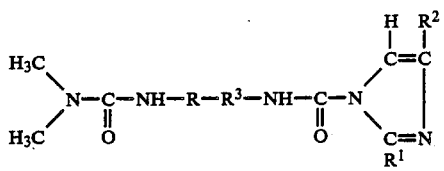

wherein the substituents are defined hereinbelow.
R is an aliphatic group, cycloaliphatic group, aryl group or araliphatic group and
$R^1$ and $R^2$ are each independently hydrogen, lower alkyl or aryl,
$R^3$ is a chemical bond or

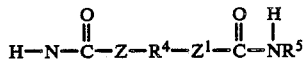

Z and $Z^1$ are independently O or NH,
$R^5$ is R,
$R^4$ is lower aliphatic, arylene, aryl lower alkylene or cycloaliphatic,
wherein the aliphatic group contains up to 10 carbon atoms in the principal chain and up to a total of 15 carbon atoms;
the cycloaliphatic group contains up to 10 ring carbon atoms and up to a total of 15 carbon atoms; and
the aryl group is an aromatic group containing from 6 to 10 ring carbon atoms and up to a total of 15 carbon atoms.

These compounds are used as accelerators in epoxy resin compositions, comprising (a) an epoxy resin, (b) dicyandiamide and optionally (c) solvents, fillers, reinforcement materials or inert materials, pigments or aids, for the production of moldings.

6 Claims, No Drawings

IMIDAZOLYL-UREA COMPOUNDS AND THEIR USE AS CURE ACCELERATORS IN EPOXY RESIN COMPOSITIONS FOR THE PRODUCTION OF MOLDINGS

This is a divisional of copending application Ser. No. 359,099, filed on May 30, 1989, U.S. Pat. No. 4,931,529, issued 6-5-90.

The invention relates to imidazolyl-urea compounds and their use as cure accelerators in epoxy resin compositions, comprising (a) an epoxy resin, (b) dicyandiamide and optionally (c) solvents, fillers, reinforcement materials or inert materials, pigments or aids, for the production of moldings.

Epoxy resins can be hardened by using the dimer of cyanamide (dicyandiamide) as a hardening agent. Two processes are currently used for compositions for production. In one process, known as the wet-in-wet process, the hardening is effected in one step. Reinforcement materials are first impregnated with a curable mixture, then are stacked in a wet stage while being shaped and finally are cured by the action of heat in one step to form the thermosetting final products.

In the other process, the hardening is effected in two steps. According to this process, so-called "prepregs" are first produced from reinforcement materials and the curable mixture, and the prepregs are further processed to finished articles in a second process step carried out at a different time. In this method, a liquid epoxy resin is converted into a solid, but still fusible B-stage resin, which is then further hardened into a non-fusible product.

The production of prepregs is normally carried out in a continuous process, in which reinforcement materials are led through an impregnation bath cf a solution of the resin-hardener mixture which is to be used. The quantity of impregnating agent which is to be applied to a particular substrate is controlled by the nip rolls fitted downstream of the impregnation bath as well as by the viscosity of the resin-hardener solution. After the impregnation process is complete, the solvent contained in the impregnation solution is evaporated by the introduction of heat and simultaneously the resin system is transformed from the A stage to the B stage. Depending upon the process conditions and the resin system used, a slightly tacky to almost dry prepreg can be produced from the impregnated reinforcement materials. It is important in this process step, that, on the one hand, the solvent of the impregnation mixture is completely removed, and on the other hand, that the latent hardener which is necessary for curing the prepreg in the second process step is not triggered, in order to prevent an undesired reaction of the impregnated reinforcement materials.

The prepregs which are obtained in this way can be temporarily stored and transported as rolls, before they are cut to the desired size and are stacked one on top of the other in the component thickness. The prepreg stack is cured by the simultaneous effects of pressure and temperature to a high-strength molding, while the still low molecular, flowable resins are being transformed into the high molecular C-stage of the thermosetting product.

The criterion for curing using the single and two step processes is that long open times and short curing times at low curing temperatures are required. Moreover, a further criterion of the two step process, is that a prepreg must be stable for storage for a long period of time. In the latter process, a storage temperature which is below room temperature is becoming less commonly used in commercial practice.

It is important that after the production of the curable mixture which is ready for use, the viscosity of the material remains substantially unchanged for the maximum amount of time.

This constant viscosity is required in order to achieve a consistent application of the resin and a constant B stage, since the production conditions cannot be continually adjusted to the varying characteristics of the curable mixture. Moreover, if the curable mixture had varying characteristics, the physical properties of the cured final products would thereby be adversely affected.

In practice, a curable mixture is sought having the following characteristics: its viscosity remains constant for a relatively long time in the impregnation bath; it converts at low temperatures in a short time to the B stage; and it can be stored as a prepreg for a long time at room temperature without chemical changes. Further, curing should be carried out at the lowest possible temperatures within a short time; the maximum temperature of the exothermic reaction should remain low even with relatively large layer thicknesses; and the physical properties of the final product should be suited to the requirements in practice. In other words, the transition temperatures determined by the matrix should be above 140° C.

Therefore, as a rule, the dicyandiamide which has long been used as a hardener in curable mixtures based on epoxy resins is combined with co-curing agents and/or accelerators in order to achieve the desired properties. A large number of proposals in this field are therefore known from the literature.

U.S. Pat. No. 1,349,709 describes a process for hardening epoxy resins using monomeric cyanamide. The subject matter and the descriptions therein are incorporated herein by reference with the same force and effect as if fully set forth herein.

The use of amine, as accelerators, e.g., tertiary amines, such as benzyl-dimethylamine, tertiary/secondary amines such as 2-methylimidazole, 2-ethyl-4-methylimidazole, or tertiary/primary amines such as 1-aminoethylimidazole singly or mixtures thereof, admittedly brought gradual improvements. But, they did not eliminate all of the deficiencies.

The use of dry monomeric cyanamide, replacing dicyandiamide, as suggested in DE-AS No. 2,122,955, was just as unattractive as the suggested associated use of aliphatic and cycloaliphatic primary monoamines or diamines containing primary and secondary amino groups.

The literature also discloses other compounds as accelerators, such as, those which contain one or two urea groups in the molecule, e.g., N,N-dimethylurea compounds (See U.S. Pat. Nos. 3,661,989, and 3,717,612) or imidazolylureas (See No. EP-A-193,068, U.S. Pat. Nos. 4,533,715 4,358,571, and 4,335,228). These references are incorporated herein by references with the same force and effect as if fully set forth herein.

The use of these compounds as accelerators alone or in combination with benzyldimethylamine or C- or N-substituted imidazoles admittedly produced improvements with regard to the storage stability or the curing characteristic or the final physical properties. But the overall level of properties of the final products still required improvements.

Thus, the object of the present invention is to find a means of overcoming the disadvantages of the prior art. In particular, the object of the present invention is to find curable mixtures based on epoxy compounds, latent curing agents and cure accelerators, wherein said mixtures are stable even in the B stage at room temperature for a long period of time, but which at the same time harden at relatively low temperatures and in short times without high exothermic temperature peaks to form the thermosetting final products. Moreover, the object of the present invention is to find a curable mixture described hereinabove, wherein its heat resistance corresponds to those which are required in practice.

This object is achieved by the addition of a cure accelerator, which contains at least two different urea components in the molecule.

More specifically, the invention relates to compounds of the general formula (I), $$\begin{array}{c} H_3C \\ \phantom{H_3}\diagdown \\ \phantom{H_3C\diagdown}N-\underset{\underset{O}{\|}}{C}-NH-R-R_3-NH-\underset{\underset{O}{\|}}{C}-N\diagup\overset{\overset{H\phantom{xx}R^2}{|\phantom{xx}|}}{\underset{\underset{R^1}{|}}{\underset{C=N}{C=C}}} \\ H_3C\diagup \end{array} \quad (I)$$

in which

R is an aliphatic, cycloaliphatic, aryl or araliphatic group, $R^1$ and $R^2$ are independently H, lower alkyl or aryl, $R^3$ is a chemical bond or $$H-\underset{\phantom{xx}}{N}-\underset{\underset{O}{\|}}{C}-Z-R^4-Z^1-\underset{\underset{O}{\|}}{C}-\underset{\underset{H}{|}}{N}R^5$$

Z and $Z^1$ are independently O or NH;

$R^5$ is R;

$R^4$ is lower aliphatic, aryl, aryl lower aliphatic or cycloaliphatic.

When $R^3$ is a chemical bond, the compound of Formula I has the formula $$\begin{array}{c} H_3C \\ \phantom{H_3}\diagdown \\ \phantom{H_3C\diagdown}N-\underset{\underset{O}{\|}}{C}-NH-R-\phantom{-}NH-\underset{\underset{O}{\|}}{C}-N\diagup\overset{\overset{H\phantom{xx}R^2}{|\phantom{xx}|}}{\underset{\underset{R^1}{|}}{\underset{C=N}{C=C}}} \\ H_3C\diagup \end{array}$$

When $R^3$ is other than a chemical bond, the compound of Formula I may contain one or more urea or urethane groups, i.e., $$\underset{\underset{}{|}}{\overset{H}{N}}-\underset{\underset{O}{\|}}{C}-Z-R^4-Z^1-\underset{\underset{O}{\|}}{C}-NH,$$

wherein Z is O or NH.

As used herein, the term, aliphatic group is an alkylene chain containing up to 10 carbon atoms which may be substituted with inert groups, such as alkyl groups, such that the total number of carbon atoms in the aliphatic group does not exceed 15. The preferred aliphatic group is lower aliphatic, i.e., the total number of carbon atoms in the lower aliphatic group contains 1–6 carbon atoms. The alkylene chain may be a straight chain or branched chain and may include such radicals, as, e.g., methylene, ethylene, isopropylene, butylene, hexylene, isobutylene, t-butylene, sec-butylene, and the like.

The term cycloaliphatic group is a cycloalkyl group containing from 3 to 10 carbon ring atoms. Moreover, said cycloaliphatic groups may be substituted with other inert groups, such as alkyl, so that the total number of carbons does not exceed 15 carbon atoms. The cycloaliphatic group may be monocylic or bicyclic. Such groups include cyclopentyl, cyclohexyl, cyclooctyl, decalinyl and the like, and the alkyl substituted groups, such as $$\begin{array}{c} H_3C\diagdown\phantom{x}\diagup CH_2- \\ \phantom{xx} \\ \phantom{xxx}\diagdown\phantom{xx}\diagup CH_3 \\ \phantom{xxxxx}CH_3 \end{array}$$

and the like.

As defined herein the term aryl is an aromatic radical containing from 6 to 10 ring carbon atoms which may be substituted by inert groups, such as alkyl groups, so that the total number of carbon atoms does not exceed 15 carbon atoms. These groups include, phenyl, α or β-naphthyl, xylyl, tolyl, and the like.

The araliphatic group as defined herein is an arylalkyl group. The alkylene and aryl groups are as defined hereinabove. Examples include benzyl, phenethyl and the like. The preferred R groups are $$\begin{array}{c} H_3C\diagdown\phantom{x}\diagup CH_2- \\ \phantom{xx} \\ \phantom{xxx}\diagdown\phantom{xx}\diagup CH_3 \\ \phantom{xxxxx}CH_3 \end{array}$$

2,4-tolyl, 2,6-tolyl, 4,4'-diphenylmethyl, hexamethylene and o-, m- or p-xylyl.

The term lower alkyl as used herein is an alkyl group containing 1–6 carbon atoms. These groups may be straight-chained or branched. These groups include methyl, ethyl, propyl, isopropyl, butyl, sec-butyl, isobutyl, tobutyl, pentyl, amyl, hexyl and the like.

The preferred $R^1$ and $R^2$ groups are hydrogen, methyl, ethyl and phenyl.

The most preferred $R^1$ group is ethyl and the most preferred $R^2$ group is methyl.

The compounds of Formula I of the present invention can be used as accelerators in curable mixtures containing:

(a) epoxy resin
(b) dicyandiamide and optionally
(c) solvents, fillers, reinforcement materials or inert materials, pigments, or aids.

The invention further relates to curable epoxy resin compositions containing (a) an epoxy resin having, on average, more than one epoxy group per molecule,
(b) dicyandiamide
(c) compounds of Formula I as cure accelerators and (d) optionally solvents, fillers, reinforcement material or insert materials, pigment, or aids.

The invention further relates to curable mixtures which are characterized in that the reinforcement materials are impregnated at room temperature with a binder, whereby said binder comprises (a) epoxy resin
(b) dicyandiamide
(c) solvent and
(d) a cure accelerator containing a compound of Formula I, which is capable of being converted into a semisolid, but still fusible B stage (resin).

The invention further relates to epoxy resin moldings, which are characterized in that in the first step the reinforcement materials are impregnated at room temperature with a binder, whereby said binder comprises (a) epoxy resin
(b) dicyandiamide
(c) solvent
(d) a cure accelerator containing a compound of Formula I, and said binder is converted into the semisolid, but still fusible B stage resin and in a second step the prepregs produced in this way are cured on their own by the application of pressure at elevated temperature to form a non-fusible product.

The epoxy resins according to the invention which are used are glycidyl esters and glycidyl ethers with two or more epoxy groups per molecule. These include, the glycidyl ethers based on monohydric or polyhydric phenols. Suitable epoxy compounds for use in the present invention are primarily polyglycidyl ethers (especially diglycidyl ethers) that are liquid at room temperature and are derivable from (i) a polyhydric phenol (especially a bisphenol), a novolak or a polyhydric alcohol (especially a diol, for example polypropylene glycol) and (ii) epichlorohydrin. (A glycidyl group is a 2,3-epoxy-propyl group). The corresponding methylglycidyl ethers (that is 2,3-epoxy-2-methyl-propyl ethers) are also suitable and may be prepared from a compound named at (i) and methylepichlorohydrin (that is 1-chloro-2,3-epoxy-1-methyl-propane).

Other suitable compounds include glycidyl esters of polycarboxylic acids (including dicarboxylic acids), especially those acids of the aromatic series (for example phthalic acid) or of the aliphatic series.

Epoxy compounds obtained by the epoxidation of olefinic compounds are also suitable. A mixture of two or more of the above-mentioned epoxy compounds may be used. Furthermore, a mixture of one or more of said compounds with an "active diluent" may be used. A monoglycidyl ether of an alcohol or phenol or a monoglycidal ester of a carboxylic acid, especially an aromatic or aliphatic carboxylic acid, is very suitable as an active diluent. Throughout this specification, the term "poly" is intended to include the term "di".

The various epoxy groups that can be utilized is described in U.S. Pat. No. 1,349,709, which is incorporated herein by reference with the same force and effect as if fully set forth herein.

Glycidyl ethers having 1,2-epoxy resins, e.g., 2,2-bis(4-hydroxy-phenyl)propane (bisphenol A) are preferred. It is preferred that said glycidyl ether have an epoxy equivalent weight ranging from 190 to 400. It is especially preferred d that the epoxy resins have epoxide values of 0.2–0.6 particularly with the compounds which are liquid at room temperature. Even more preferred epoxy resins have epoxide values ranging from 0.45 to 0.55. Additionally, glycidyl ethers based on bisphenol F and the Novolak resins have also proved advantageous.

The dicyandiamide which is co-used as curing agent is a commercially available product and is obtainable under known trade names. The quantity of dicyandiamide, depending on the epoxy compound used, is in the range of 2 to 10 parts per weight per 100 parts by weight of diglycidyl ether. When the preferred liquid glycidyl ethers, such as bisphenol A, are used, the amount of dicyandiamide used is in the range of 5 to 10 parts by weight, based on 100 parts by weight of diglycidyl ether.

The cure accelerators which are co-used according to the invention are compounds of the general Formula (I), wherein R, $R^1$ and $R^2$ are defined hereinabove.

The cure accelerators can be formed by procedures which are known to one skilled in the art. For example, the compounds of formula (I) can be produced by reacting an isocyanate of the formula

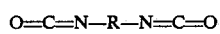

$$O=C=N-R-N=C=O \qquad II$$

with an imidazole of the formula

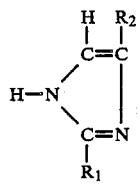

III and dimethylamine where R, $R^1$ and $R^2$ are as described above, under imidazolyl urea forming conditions. The imidazole is first added to the reaction mixture, followed almost immediately thereafter with dimethylamine to form the compounds of Formula I.

It is also possible to use prepolymers of the diisocyanates containing urethane groups or urea groups instead of the diisocyanates. In the case of isophorone diisocyanates, the more reactive isocyanate group is already to a large extent converted by a preliminary reaction of this kind with the hydroxyl group, so that the less reactive isocyanate group participates preferentially in the subsequent reaction with the amine components. The reaction of the isocyanates with the imidazoles and the dimethylamines is preferably carried out in a solvent, which can also dissolve dicyandiamide, so that a mixture is obtained which is ready for use for the production of prepreg.

Products formed may contain some byproducts but they may be used as accelerators, without purification. It is also possible to have mixtures of the individual pure components in each case.

Various isocyanates can be used. However, these isocyanates must have at least two isocyanate groups for reaction with the amines. Preferred groups are:

Isophorone diisocyanate (IPDI), tolylene diisocyanate (TDI), such as 2,4-tolylene diisocyanate, 2,6-tolylene diisocyanate, diphenylmethane diisocyanate (MDI), such as 4,4'-diphenylmethane diisocyanate, hexamethylene diisocyanate (HDI), trimethylhexamethylene diisocyanate (TMDI), xylylene diisocyanate (XDI), tetramethyl xylylenediisocyanate (TMXDI) and mixtures of these, as well as the products of dimerization and trimerization of the corresponding isocyanates. Other diisocyanates that could be used include orthophenylene diisocyanate, metaphenylene diisocyanate, paraphenylene diisocyanate, or isomeric mixtures thereof, 3,3'-dimethyl-4,4'-biphenyl diisocyanate and the like.

Alternatively, the diisocyanate adduct can be extended prior to reacting with the imidazole and the dimethylamine. For example, the diisocyanate can be reacted with alcohols to form the corresponding prepolymer isocyanates containing one or more urea or urethan groups with residual isocyanate groups which in turn can react with the imidazole of Formula III and the dimethylamine. Using this method, it is preferred that a diol be used and that the molar ratio of diisocyanate to diol be 2:1. For example, the isophoronodiisocyanate is reacted with butanediol in a molar of 2:1 and the product formed therefrom is reacted with imidazole and dimethylamine to form the product of Formula I, wherein R is

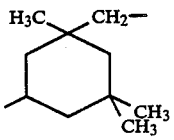

The imidazoles utilizable in this invention are known and many are commercially available. Typical imidazole include imidazole, 2-methyl-imidazole, 2-ethylimidazole, 2,4-diethylimidazole, 2-ethyl 4-methylimidazole, 2,4,5-trimethylimidazole, 2-benzylimidazole, 4-methylimidazole, 2-phenylimidazole.

The preferred imidazoles are 2-methylimidazole and 2-ethyl-4-methylimidazole.

The quantity of cure accelerator can be varied within wide limits. It is determined by the intended application and the curing conditions which may thus be prescribed. According to the invention, quantities in the range of 0.1 to 10, preferably 1 to 5 parts by weight, based on 100 parts by weight of epoxy compound are used.

In the one process step, anhydrous dicyandiamide is dissolved in the epoxy compound at abouit 50° C. If the solution so formed is then left to stand at room temperature, it may remain unchanged for several days or even weeks depending on the stability of the dicyandiamide and the impurities present in the resin. After the expiry of this "initiation period", the solution is in the form of a layer not more than about 1 cm thick, this spontaneous hardening will result in the formation of a B-stage product. However, if the solution is in the form of a large batch, the hardening will result in the formation of a non-fusible product, without an intermediate B-stage product being formed. The reason for this is that the reaction between the resin and the dicyandiamide is strongly exothermic. If the heat formed can be dissipated rapidly enough, for example, by using only a thin layer of solution, the intermediate B-stage product will be formed, whereas if the heat accumulates in the solution it will cause the reaction to proceed right through to the final non-fusible product. A further method of dissipating the heat is to add a filler to the solution.

If it has not already become hardened, the solution may be hardened when desired by heating it to from 100° to 200° C.

The quasi-latent system described above may be used in practice for a variety of purposes. For example, it may be used to produce glass-fibre reinforced plastics materials, for example shaped components, panels, tubes, bonds or coatings, directly from the liquid phase by heating to a temperature of from 100° to 200° C. It can also be used for the manufacture of casting resins, provided that excessive heat accumulation is prevented as this might cause fissuring or even charring; this can generally be avoided by adding a filler or by using other means to dissipate the heat.

The reaction between the epoxy compound and the dicyandiamide can be "catalyzed" by the use of a small quantitiy of cure accelerator according to the present invention. This results in a decrease in the time and/or temperature needed for hardening, with a consequent decrease in the length of the "initiation period" and thus of the pot-life of the solution.

Instead of hardening the dicyandiamide/resin mixture in one step as described above, by heating it to from 100° to 200° C., the mixture may be hardened in two steps: in a first step a mixture of an epoxy resin and anhydrous dicyandiamide is converted at a temperature of from 20° to 160° C. into a solid, but still fusible, B-stage product, and this is then cured, in a second step, at from 100° to 200° C. The formation of the B-stage product may take several days if a relatively low temperature is used but may only take a few minutes if a higher temperature is used. The accelerator of the present invention is preferably added to the mixture in order that the B-stage product may be formed within an acceptable period.

The compositions of the invention can additionally comprise one or more fillers, reinforcing agents (for example fibres or fabrics), pigments and other adjuvants.

In order to modify the properties of the final product, in addition to other epoxy resins, modifiers or aids can also be co-used such as phenolic resins, melamine resins, silicone resins, or inorganic and organic fillers such as powdered quartz, titanium dioxide, carbon black, silicone rubber or butadiene rubber or additives such as pigments and colorants. Fillers may be generally used to increase performance at high temperature, reduce the coeffecient of thermal expansion, increase thermal conductivity, decrease skrinkage (by reducing peak exotherm temperature) and alter moisture resistance. Suitable fillers include calcium, carbonate, talc, aluminum oxide, flint powder, silica, mica, and metallic powders (Al, Zn, and the like).

Common pigments that may be used include titanium dioxide, aluminum powder, carbon black, and cadmium red medium and codmolith golden, both produced by The Chemical and Pigment Co.

To adjust to the desired viscosity, resins of different viscosity or (reactive) diluents can be added. Moreover, inert but volatile solvents can also be added. These include dimethyl formamide, acetone, methylglycol or mixtures of these.

In order to produce the prepregs, organic and inorganic fibers, fibre mats or fabrics based on aramides, carbon or cellulose, metals such as boron, steel, and so on, or ceramics, particularly glass, may be impregnated with the epoxy dicyandiamide/accelerator mixture, in accordance with the procedure described hereinabove, and these are converted to a B-stage product at room temperature or at elevated temperatures.

The production of the prepregs is carried out in accordance with methods known per se, in which the reinforcement materials or the substrate materials are soaked in an impregnation bath with the reactive resin mixture and after nipping off the excess quantity of resin they are continuously converted from the A stage to the B-stage product by the introduction of energy (mostly heat), with simultaneous removal of the solvent which may optionally be present. Depending on the desired prepreg consistency (tacky to solid), the prepregs are subsequently provided on both sides with a release film and are rolled up for storage and transport. Further processing is carried out by cutting the individual layers of prepreg to size and laying them together to form a stack, from which a highly cross-linked component is produced by shaping procedures with the simultaneous introduction of heat.

The accelerators according to the invention can moreover be successfully used in solvent-free systems based on dicyandiamide and epoxy resins. A typical field of application is the use of hot-curing single component adhesives for the bonding of body components in the automobile industry (seam beading cement).

A thermosetting composition may be prepared from the above-mentioned preferred preparation of the invention by converting the preparation into a B-stage product at from 20° to 160° C. and then (if a temperature above room temperature has been used) cooling the product. In some circumstances it may be necessary to use rapid cooling in order to prevent the B-stage product becoming converted into a non-fusible product within, for example, 24 hours. It is necessary to prevent the formation of cross-linked products by heat accumulation. When the filler (for example glass fibre) content is fairly high, as is usually the case in formulation moulding compositions or prepregs, the inorganic filler material is generally capable of absorbing the heat of reaction. When the filler content is low, or the composition is unfilled, as, for example, in the manufacture of powder lacquers, heat accumulation can be prevented by allowing the composition to solidify in flat dishes in not too thick a layer.

The heat-curable epoxy resin compositions obtained in this manner can be further processed, with or without fillers and the like, in the form of, for example, adhesives, coatings or moulding compositions.

One especially noteworthy advantage of the invention is that it enables powder lacquer formulations to be prepared on normal roller mills at room temperature instead of with special extruders at elevated temperatures as has hitherto been necessary.

The following Examples further illustrate the invention.

EXAMPLE I

Production of an accelerator according to the invention from isophorone diisocyanate (IPDI), 2-ethyl-4-methylimidazole (EMI 2,4) and dimethylamine 111 g IPDI (0.5 mol) are preheated in 111 ml of carbon tetrachloride under nitrogen to about 40° C. A solution of 55 g (EMI 2,4) (0.5 mol) in 55 ml of carbon tetrachloride is added with stirring over 1 hour. A temperature of 40°-50° C. is maintained for about 2 hours and, after cooling to room temperature, 22.5 g of dimethylamine (0.5 mol) is added. A highly viscous yellow solution is produced, which is freed from solvent at about 50° C. in vacuo. The reaction product has a softening point of about 82° C. and shows no N=C=O bands in the IR spectrum. It is soluble in acetone, methyl ethyl ketone, methylene chloride, carbon tetrachloride and propylene glycol monomethyl ether.

EXAMPLE IA

Production of a prepreg mixture from I without the co-use of dicyandiamide

The accelerator according to the invention is mixed at room temperature (RT) with dimethylformamide in a ratio of 1:5 by weight. An impregnation mixture suitable for the production of prepregs is produced from 60 parts by weight of this accelerator solution by addition of 100 parts by weight of a medium viscosity epoxy resin (weight of one equivalent of epoxide, about 190).

In order to produce prepregs on the laboratory scale, a glass filament fabric about 0.1 m$^2$ in size, in the sateen weave (296 g/m$^2$) is soaked in the impregnation mixture and subsequently given heat treatment for 5 minutes at 100° C. in the forced-air oven. Flexible, but highly tacky and thus scarcely manipulable prepregs are obtained with a resin content of about 30% by weight, which do not change significantly in consistency even after several days storage between polyethylene films.

After a temporary storage of at least 24 hours, 2 prepreg layers in each case are pressed by hot press molding at 120° C. and 0.1 bar for 30 minutes. The final product has an exceptionally low rigidity for glass fabric reinforced EP resin systems. The transition temperature determined from the torsion pendulum test (DIN 53445) is 65° C. The procedure from the torsion pendulum is described in said reference and the procedure therein is incorporated by reference with the same force and effect as if fully set forth herein.

EXAMPLE II

Production of an accelerator according to the invention from isophorone diisocyanate, 2-ethyl-4-methylimidazole and dimethylamine in dimethyl formamide (DMF)

55.5 g IPDI (0.25 mol) are preheated in 55.5 g of dimetyl formamide under nitrogen to about 40° C. A solution of 27.5 g EMI 2.4 (0.25 mol) in 27.5 g of dimethyl formamide is added with stirring over 1 hour. A temperature of 40°-50° C. is maintained for about 2 hours and after cooling to room temperature, 11.25 g of dimethylamine (0.25 mol) is run in.

The reaction product is a solution of about 50% strength in dimethyl formamide and shows N=C=O bands in the IR spectrum.

EXAMPLE IIA

Production of a prepreg reaction mixture from II with the co-use of dicyandiamide The solution of:
24 g of dicyandiamide and
21 g of reaction product II in
135 g of dimethyl formamide
is mixed to a concentration of 60 parts per 100 parts of resin with an epoxy resin (weight of one equivalent of epoxide, about 190) and used for the production of prepregs. The viscosity of this impregnation solution, measured with a cone and plate rheometer at 20° C. (supplier Epprecht Instruments), is 0.09 Pa.s and does not measurably change with storage at room temperature even after several days.

When used for the production of prepregs as described under point Ia. and the curing time is altered from 5 minutes to 10 minutes, flexible, slightly tacky products are obtained. These can be cured to form thermoset moldings even after storage at room temperature between polyethylene films for more than 4 weeks, without loss of properties. The transition temperature of the cured products, determined by the torison pendulum test in accordance with DIN 53445 is 156° C. and this value is not reduced even after storage of the test pieces at 60° C. for 90 hours.

EXAMPLE IIb

Production of a prepreg reaction mixture from II without co-use of dicyandiamide The accelerator according to the invention is mixed at room temperature with dimethyl formamide in the ratio 2:4 by weight. An impregnation mixture which can be used for the production of prepregs is produced from 60 parts by weight of this accelerator solution by addition of 100 parts by weight of a medium viscosity epoxy resin (weight of one equivalent of epoxide, about 190), and this impregnation mixture is processed as described in EXAMPLE IA. The transition temperature determined from the torsion pendulum test (DIN 53445) is also at the level cf EXAMPLE IA.

EXAMPLE III

The production of an accelerator from butanediol, isophorone diisocyanate, 2-ethyl-4-methylimidazole and dimethylamine)

0 88.8 g of IPDI (0.4 mol) are preheated in 97.8 g of dimethyl formamide under nitrogen to about 75° C. 18.0 g of 1,4-butanediol (0.2 mol) in 18 g of dimethyl formamide are added dropwise and the reaction mixture kept at 75° C. for about 1.5 hours. After cooling to room temperature, 22.0 g of EMI 2,4 (0.2 mol) in 22 g of dimethyl formamide are added over 30 minutes. Subsequently 9.0 g of dimethylamine (0.2 mol) are run in at room temperature.

The reaction mixture is a 50% strength solution in dimethyl formamide and shows no N=C=O bands in the IR spectrum.

EXAMPLE IIIA

Production of a prepreg reaction mixture from III with the co-use of dicyandiamide The solution comprising
24 g of dicyandiamide and
24 g of reaction product III in
132 g of dimethyl formamide
is mixed to a concentration of 60 parts per 100 parts of resin with an epoxy resin (weight of one equivalent of epoxide, about 190) and used for the production of prepregs.

The viscosity of the impregnation solution measured with the cone and plate rheometer is 0.10 Pa.s at 20° C. In the case of the (flexible, slightly tacky) prepreg produced according to EXAMPLE IA. and further processed after a 4-week temporary storage at room temperature, a transition temperature of 143° C. is determined in the torsion pendulum test (DIN 53445).

For exact comparison of the accelerators according to the invention with the accelerators according to the state of the art, dicyandiamide/accelerator formulations were prepared, in which the total nitrogen content of the accelerator components was calculated to have the same value.

EXAMPLE IV

The 50% strength solution described in EXAMPLE II of the reaction product from 1 mol of IPDI with 1 mol of 2-ethyl-4-methylimidazole and 1 mol of dimethylamine is used in the following formulation:
4.0 g of dicyandiamide
2.9 g of solution II, containing 1,45 g of accelerator (18.6% N),
23.1 g of dimethyl formamide (analytically pure).

This solution is mixed to a concentration of 60 parts to per hundred parts of resin with an epoxy resin (weight of one equivalent of epoxide, about 190). Test results are given in Table I.

EXAMPLE V

V. N,N-dimethyl-N'-phenylurea is produced by a known process from equivalent quantities of phenylisocyanate and dimethylamine. After recrystallization from water the product has a melting point of 134° C. The N-content is 17.1%

The following dicyandiamide accelerator solution is produced from this product.
4.0 g of dicyandiamide
1.5 g of N,N-dimethyl-N'-phenylurea (17.1%N)
24.5 g of dimethyl formamide (analytically pure)

This solution is mixed to a concentration of 60 parts per hundred parts of resin with an epoxy resin (weight of one equivalent of epoxide, about 190). Test results are given in Table I.

EXAMPLE VI 111 g of IPDI (0.5 mol) are dissolved in 111 ml of acetone (analytically pure). The solution is heated to 50°–60° C. under nitrogen and slowly mixed with 110 g of 2-ethyl-4-methylimidazole (1 mol) dissolved in 110 ml of acetone (analytically pure). The temperature is kept at 50°–60° C. for about 3 hours, so that no N=C=O bands remain detectable in the IR spectrum. After removal of the acetone a solid is obtained. The N-content is 19.0%.

The following dicyandiamide accelerator solution is produced from this product:
4.0 g of dicyandiamide
1.35 g of the product VI
24.65 g of dimethyl formamide (analytically pure)

This solution is mixed to a concentration of 60 parts per hundred parts of resin with an epoxy resin (weight of one equivalent of epoxide, about 190). Test results are given in Table I.

| | | Material characteristics at concentrations of accelerator which are equal in respect of total nitrogen content | | | | | |
|---|---|---|---|---|---|---|---|
| | | Viscosity of the impregnation solu/20° C. | | | Kick-off temperature | Reaction duration at 120° C. | Transition temperature by Torsion Pendulum Test (DIN 53445) |
| Example | Patent Status | upon being produced | after 6 days storage at RT | Increase | by DSC measurement | | |
| IV | according to the invention | 80 m Pa. s | 80 m Pa. s | 0% | 132° C. | 23 min. | 151° C. |

-continued

| Example | Patent Status | Viscosity of the impregnation solu/20° C. | | Increase | Kick-off temperature by DSC measurement | Reaction duration at 120° C. | Transition temperature by Torsion Pendulum Test (DIN 53445) |
|---|---|---|---|---|---|---|---|
| | | upon being produced | after 6 days storage at RT | | | | |
| V | not according to the invention | 70 m Pa. s | 70 m Pa. s | 0% | 135° C. | 22.4 min | 137° C. |
| VI | not according to the invention | 80 m Pa. s | 150 m Pa. s | 88% | 98° C. | 15 min. | 152° C. |

The viscosities of the impregnation solutions, shown in the Table I, were obtained as given above at 20° C. with a cone and plate rheometer, the solutions being stored in a closed vessel at room temperature for 6 days between the 1st and 2nd measurement.

The kick-off temperatures which are also shown in the table were determined by DSC (apparatus TA 3000 supplied by Mettler) on freshly prepared impregnation solutions starting from a temperature of 10° C. with a heating rate of 20° C./min. The duration of the reaction of the various impregnation solutions which is given results from the analysis of the kinetics, which was carried out by DSC measurements on these products at a heating rate of 1° C./min.

The transition temperatures were determined in the torsion pendulum test in accordance with DIN 53445 using a heating rate of 1° C./min., the test pieces, as described in EXAMPLE IA. being first of all formed into prepregs and subsequently cured to form thermosets.

The results of these test are tabulated in Table I.

The above embodiments and examples are given to illustrate the scope and spirit of the present invention. These embodiments and examples will make apparent, to those skilled in the art, other embodiments and example. The other embodiments and examples are with the contemplation of the present invention. Therefore, the present invention should be limited only by the appended claims.

What is claimed is:

1. A process for preparing a curable mixture which may be cured subsequently to prepare epoxy resin moldings comprising impregnating reinforcement materials with a binder at room temperature, said binder comprising a curing effective amount of an epoxy resin and a dicyandiamide in the presence of a catalytically effective amount of an accelerator compound in an inert solvent and heating the product therefrom into a semi-solid but fusible B-stage resin, said accelerator compound having the formula

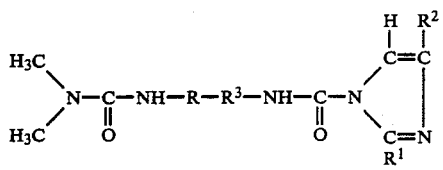

wherein
R is an aliphatic group, a cycloaliphatic group, an aryl group, or an araliphatic group;
$R^1$ and $R_2$ are each independently hydrogen, lower alkyl or aryl,
$R^3$ is a chemical bond or

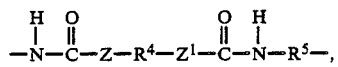

wherein Z and $Z^1$ are independently O or NH;
$R^5$ is R; and
$R^4$ is lower aliphatic, arylene, aryl lower alkylene or cycloaliphatic,
wherein the aliphatic group contains up to 10 carbon atoms in the principal chain and up to a total of 15 carbon atoms;
the cycloaliphatic group contains up to 10 ring carbon atoms and up to a total of 15 carbon atoms; and
the aryl group is an aromatic group containing from 6 to 10 ring carbon atoms and up to a total of 15 carbon atoms.

2. A process according to claim 1 including the following additional step to provide epoxy resin moldings:
curing the semi-solid but fusible B-stage resin by applying sufficient heat and pressure to form a non-fusible product.

3. A process according to claim 1 or 2 wherein $R^1$ and $R^2$ are independently hydrogen, methyl, ethyl or phenyl.

4. A process according to claim 1 or 2 wherein R is

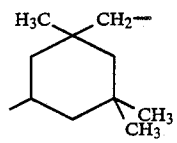

2,4-tolyl, 2,6-tolyl, 4,4'-diphenylmethyl, hexamethylene and o-, m-, or p-xylyl.

5. A process according to claim 1 or 2 wherein R is

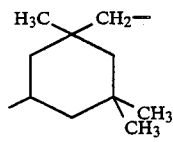

and $R^1$ and $R^2$ are independently hydrogen, methyl, ethyl or phenyl.

6. A process according to claim 1 or 2 wherein R is

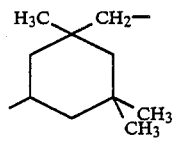

and $R^1$ is ethyl and $R^2$ is methyl.

* * * * *

UNITED STATES PATENT AND TRADEMARK OFFICE
CERTIFICATE OF CORRECTION

PATENT NO. : 4,968,732

DATED : November 6, 1990

INVENTOR(S) : Christian Burba, et al.

It is certified that error appears in the above-identified patent and that said Letters Patent is hereby corrected as shown below:

Column 1, line 36: "cf" should read as --of--

Column 5, line 64: after "preferred" delete --d--

Column 11, line 25: "cf" should read as --of--

Column 11, line 30: after "dimethylamine" delete --)--

Column 13, line 67: "$R_2$" should read as --$R^2$--

Signed and Sealed this

Seventh Day of April, 1992

Attest:

HARRY F. MANBECK, JR.

Attesting Officer

Commissioner of Patents and Trademarks